United States Patent
Nagai et al.

(10) Patent No.: US 8,198,478 B2
(45) Date of Patent: Jun. 12, 2012

(54) METHOD OF PRODUCING ALPHA-FORM GLUTAMIC ACID CRYSTALS

(75) Inventors: Hidetada Nagai, Kawasaki (JP);
Yoshifumi Takahashi, Kawasaki (JP);
Takao Yamane, Kawasaki (JP);
Nobuharu Konishi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 181 days.

(21) Appl. No.: 12/618,051

(22) Filed: Nov. 13, 2009

(65) Prior Publication Data

US 2010/0094048 A1     Apr. 15, 2010

Related U.S. Application Data

(63) Continuation of application No. PCT/JP2008/058567, filed on May 8, 2008.

(30) Foreign Application Priority Data

May 14, 2007   (JP) .................... 2007-127524

(51) Int. Cl.
   *C07C 229/24*          (2006.01)
(52) U.S. Cl. ........................................ 562/573
(58) Field of Classification Search .............. None
   See application file for complete search history.

(56) References Cited

U.S. PATENT DOCUMENTS 2,306,646 A * 12/1942 Shildneck ............ 562/573
2,584,731 A *  2/1952 Ogawa .................. 562/573

FOREIGN PATENT DOCUMENTS

| CN | 1312245 | * | 2/2001 |
| CN | 1312245 |   | 9/2001 |
| EP | 1118942 |   | 7/1968 |

OTHER PUBLICATIONS

Korovessi et al, Batch Processes, §6.8.3 L-Glutamic Acid, 2006, CRC Press, pp. 192-198.*
International Search Report for PCT Patent App. No. PCT/JP2008/058567 (Jun. 3, 2008), and published as part of EP2163539.
International Preliminary Report on Patentability for PCT Patent App. No. PCT/JP2008/058567 (Nov. 24, 2009).

* cited by examiner

*Primary Examiner* — Paul A Zucker
(74) *Attorney, Agent, or Firm* — Shelly Guest Cermak; Cermak Nakajima LLP

(57) ABSTRACT

This present invention provides crystallization of α-form crystals preferentially which are metastable crystals without precipitating β-form crystals. This method allows for the precipitation of α-form crystals which are metastable crystals by combining (a) the process of achieving supersaturation by mixing an acidic solution with an aqueous solution containing glutamic acid to attain a pH at the isoelectric point of glutamic acid or lower, and (b) after a certain elapsed time, adding more of the aqueous glutamic acid solution to achieve a second supersaturation.

4 Claims, 6 Drawing Sheets

[Fig. 1]
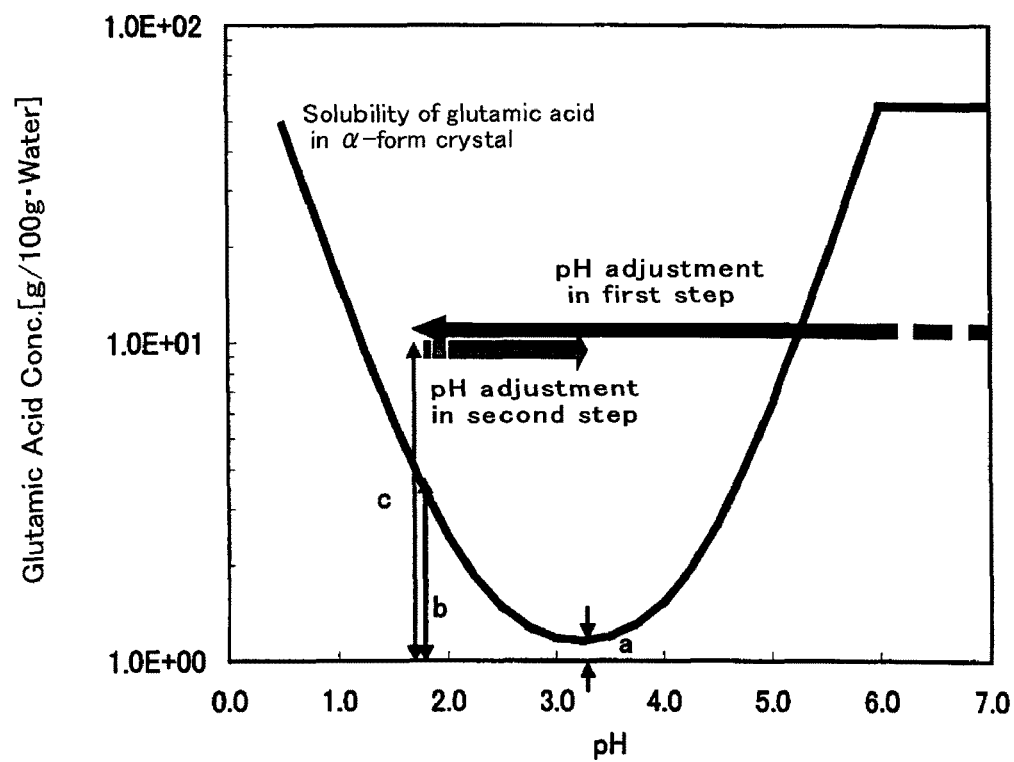

[Fig. 2]
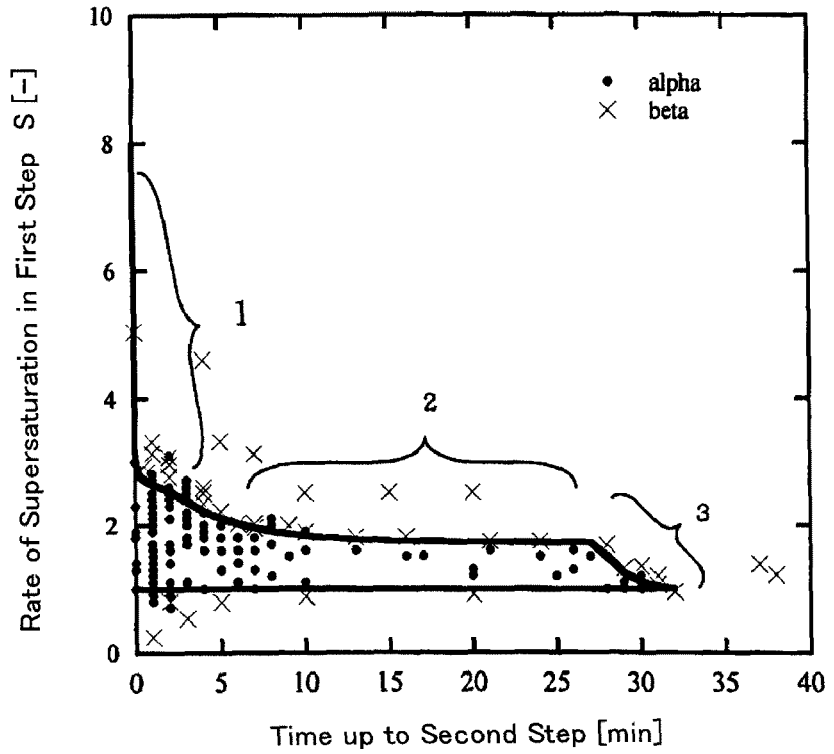
[Fig. 3]
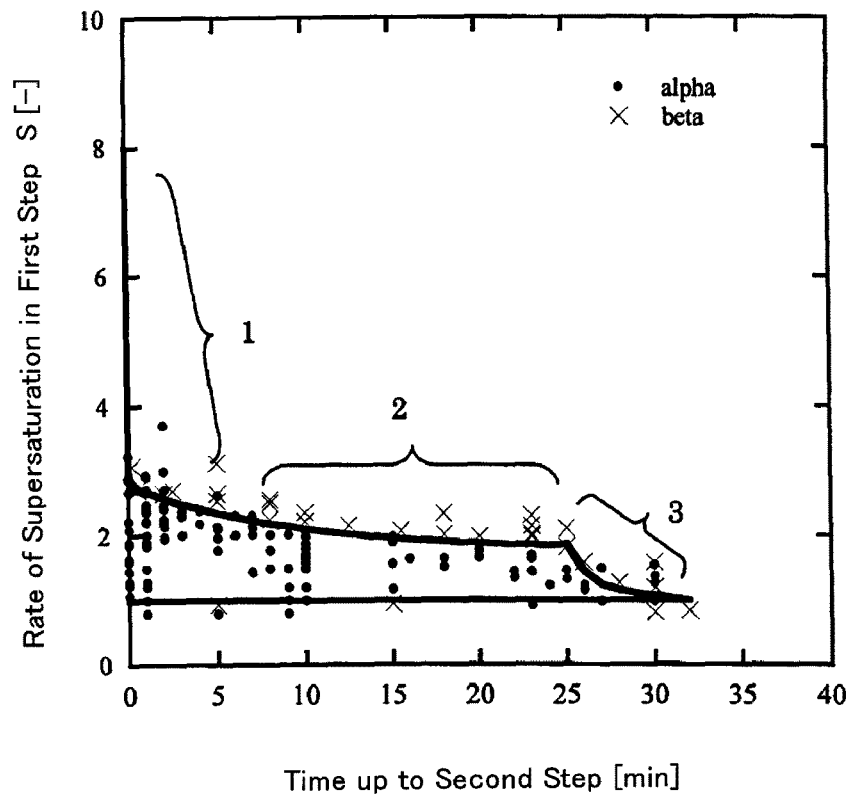

[Fig. 4]
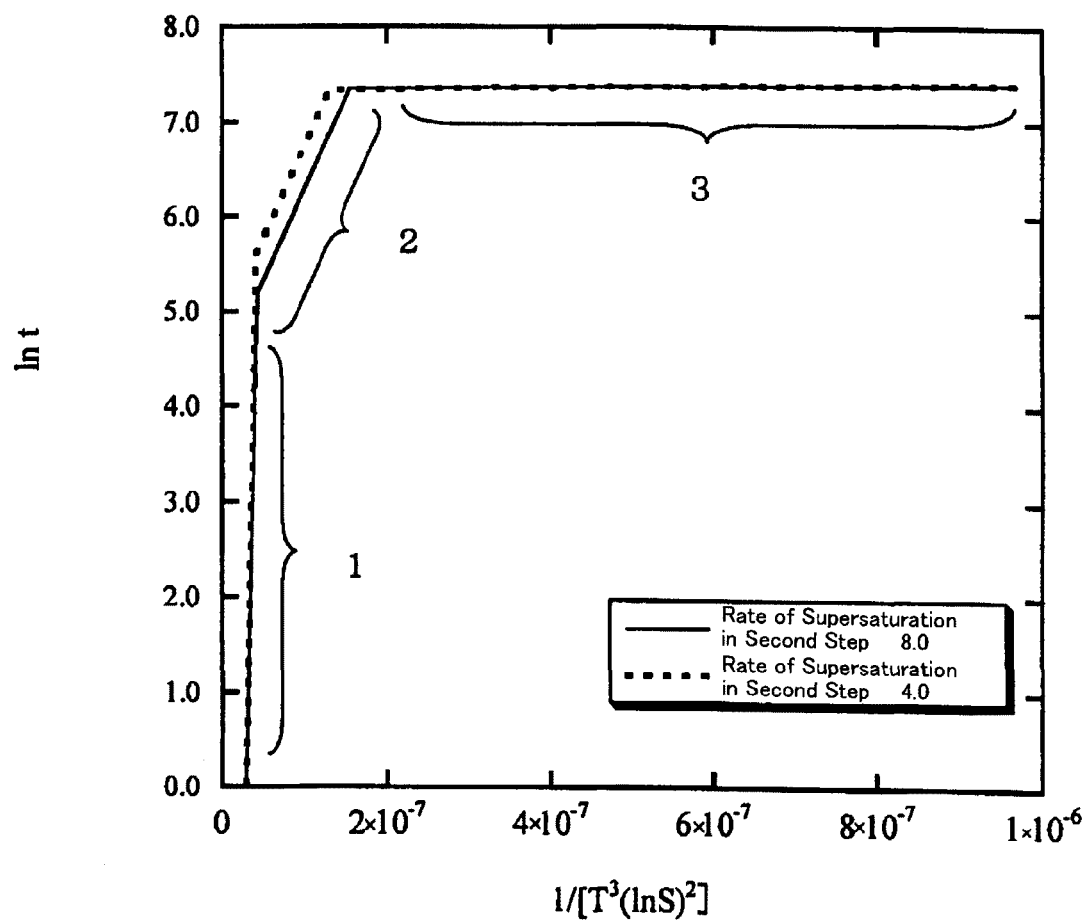

[Fig. 5]
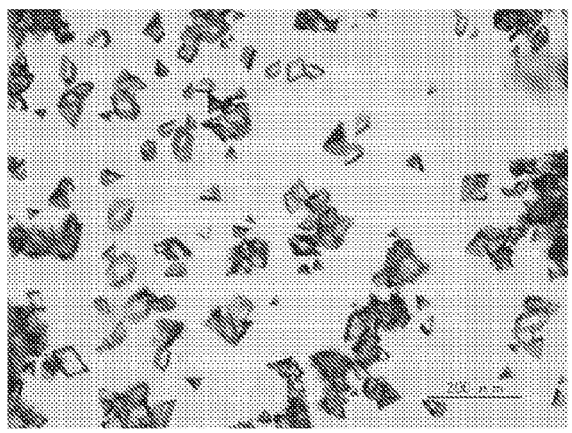
(a) Glutamic acid crystals produced in Example 1 (α-form crystals alone)
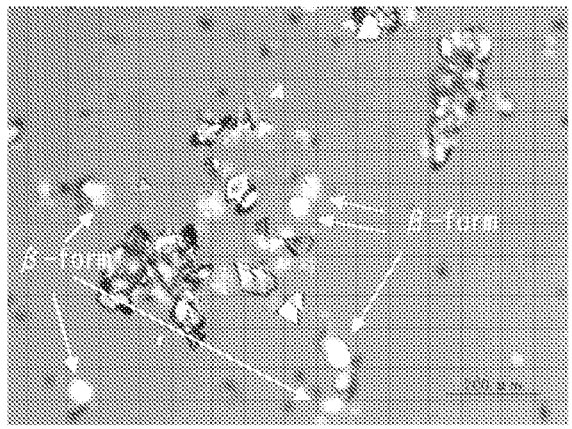
(b) Glutamic acid crystals produced in Comparative Example 1 (mixture of α-form crystals and β-form crystals; white fuzzy crystalline matters are β-form crystals)

[Fig. 6]
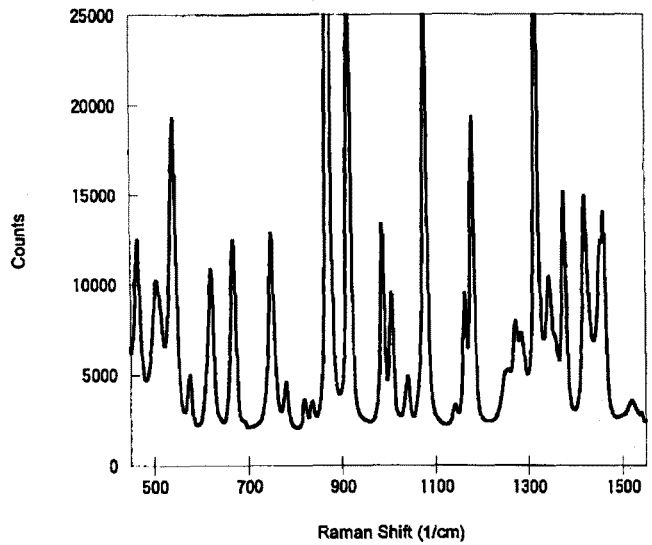
(a) Glutamic acid crystals produced in Example 1 ($\alpha$-form crystals alone)
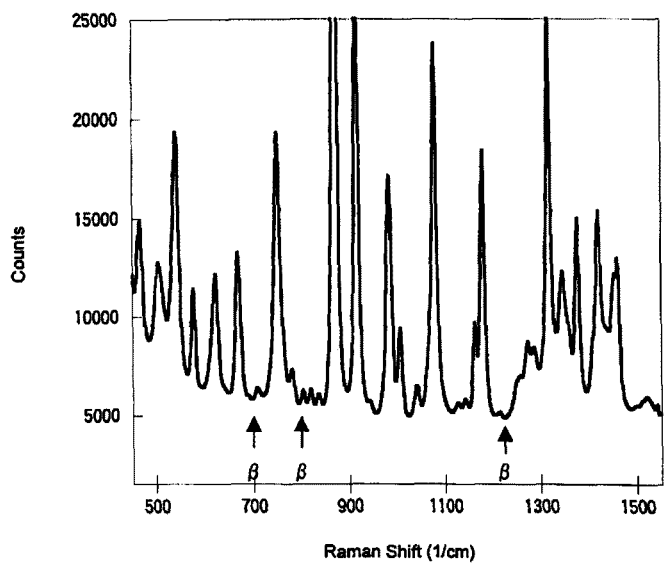
(b) Glutamic acid crystals produced in Comparative Example 1 (mixture of $\alpha$-form crystals and $\beta$-form crystals; white fuzzy crystalline matters are $\beta$-form crystals)

[Fig. 7]
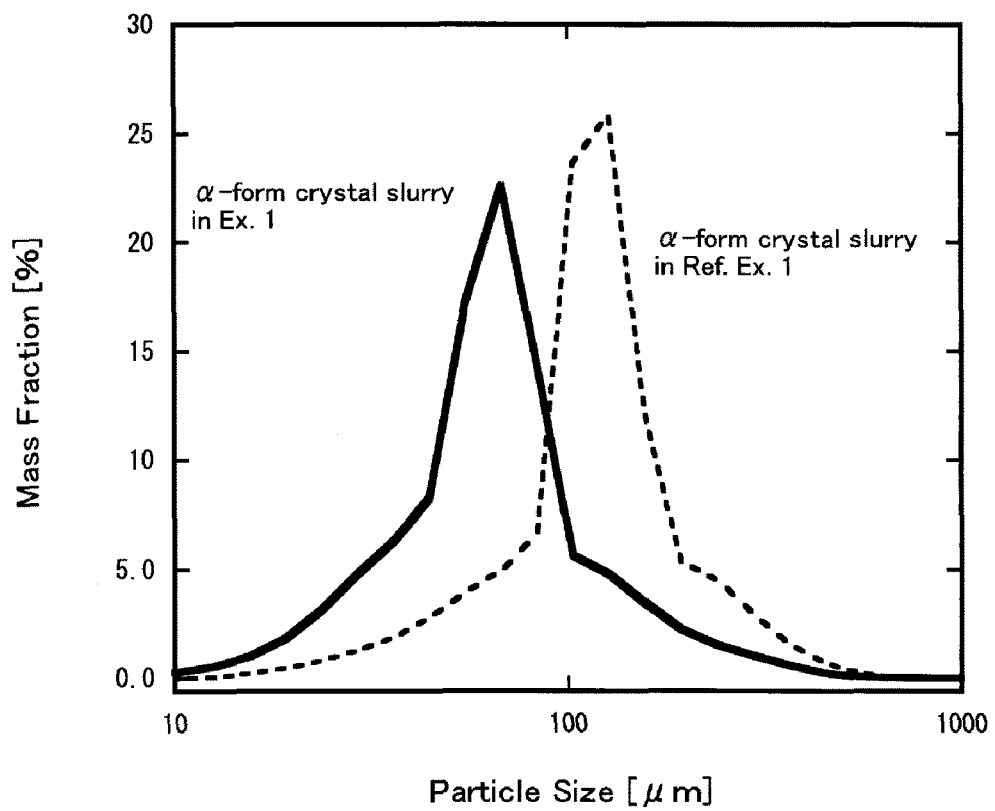

METHOD OF PRODUCING ALPHA-FORM GLUTAMIC ACID CRYSTALS

This application is a continuation under 35 U.S.C. §120 of PCT Patent Application No. PCT/JP2008/058567, filed May 8, 2008, which claims priority under 35 U.S.C. §119 to Japanese Patent Application No. 2007-127524, filed on May 14, 2007, which are incorporated in their entireties by reference.

BACKGROUND OF THE INVENTION

1. Field of the Invention

This invention relates to a crystallization method for polymorphic glutamic acid crystals which preferentially produces metastable α-form crystals.

2. Brief Description of the Related Art

Glutamic acid crystals are polymorphic, that is, two forms exist of these crystals. One form is an α-form which is metastable, and the other is a β-form which is stable.

The existence of α-form crystals has been known for a long time (JP36-017712B). Methods are also known for purifying glutamic acid by first precipating the α-form crystals, and then converting them to β-form crystals (JP45-004730B). This conversion is thought to occur due to impurities in α-form crystals that are released.

To produce α-form crystals, it has been reported that a supersaturated state can be achieved by adding an acid to a glutamic acid salt solution, resulting in a decrease in solubility of glutamic acid. Then, α-form crystals can be added as seed crystals. This method is similar to a methods employed for producing glycine crystals, wherein α-form crystals are added (N. Doki et al., Crystal Growth & Design, 4(5), 949-953, 2004). α-form crystals can also be produced by adding amino acids or sugars (JP36-017712B, JP45-011286B). In addition, it is known that α-form crystals are precipitated first upon reaching supersaturation, and then the crystals can stand without adding seed crystals (Jochen Scholl et al., Chem. Eng. Technol. 29(2), 257-264, 2006). However, a crystallization method of preferentially producing only α-form crystals by utilizing this phenomenon has not been reported.

Incidentally, the conventional method of producing α-form crystals by adding seed crystals has several problems. For example, it is difficult to store prepared seed crystals so that they do not convert to β-form crystals, due to moisture which adheres to the separated crystals. Also, it is difficult to control a glutamic acid salt solution to a particular rate of supersaturation, because in the range of pH 4-6, solubility of glutamic acid is highly sensitive to changes in pH. That is, when adjusting the pH, and the pH becomes lower than desired due to adding the acid too quickly, stable β-form crystals will precipitate due to the high rate of achieving supersaturation. Whereas, when the pH becomes too high, the added seed crystals are dissolved, and accordingly, the seed crystals are not effective at all, which also results in the precipitation of β-form crystals.

Finally, producing α-form crystals by adding amino acids or sugars results in the addition of impurities to the system, and accordingly, it does not meet the objectives of purification wherein the removal of impurities is a primary function of crystallization.

SUMMARY OF THE INVENTION

It is, therefore, one aspect of the present invention to provide a neutralization crystallization method for preferentially and firstly precipitating α-form crystals, which are metastable, with good reproducibility and without precipitating stable β-form crystals, and without adding α-form seed crystals or additives to initiate crystallization.

In neutralization crystallization to precipitate α-form crystals, there are several ways β-form crystals are also formed and precipitated. First, β-form crystals precipitate independently and are generated as primary nuclei from the solution phase, even when α-form crystals are also precipitating. Also, once α-form crystals precipitate, they are then converted into β-form crystals. Furthermore, the precipiated α-form crystals induce secondary nuclei generation of β-form crystals as seed crystals. The formation and precipitation of these crystals has been investigated, and it has been found that in solutions with a low rate of achieving supersaturation (1.0-1.7), crystals are precipitated. As a result, precipitation of α-form crystals was determined and simultaneously, β-form crystals were also observed not in the vicinity of the α-form crystals, but in the bulk solution phase. Therefore, it was deduced that β-form crystals precipitate independently from the solution phase by primary nuclei generation. Therefore, it is possible to prevent the precipitation of β-form crystals by precipitating the α-form crystals, and allowing the supersaturated state of the solution to revert to not being supersaturated prior to the precipitation of β-form crystals.

It is an aspect of the present invention to provide a method of producing α-form glutamic acid crystals comprising: (A) adding an acid to a glutamic acid salt solution until the pH of the solution is below the isoelectric point of glutamic acid and the solution is in a first supersaturated state; and (B) adding a glutamic acid salt solution until the pH of the solution rises to the isoelectric point of glutamic acid and the solution has reached a second supersaturated state.

It is a further aspect of the present invention to provide the method as described above, wherein said adding in step (B) occurs within a crystallization waiting period (t) selected from the group consisting of: (i) when the rate of supersaturation in the first supersaturated state is in the range from 2.6 to 8.0, $t \leq \exp\{1/(T^3(\ln S)^2) \times 3.46 \times 10^8 - 9.69\}$; (ii) when the rate of supersaturation in the first supersaturated state is in the range from 1.7 to 2.6, $t \leq \exp\{1/(T^3(\ln S)^2) \times 1.95 \times 10^7 + 4.35\}$; and (iii) when the rate of supersaturation in the first supersaturated state is in the range from 1.0 to 1.7, $t \leq \exp\{1/(T^3(\ln S)^2) \times 6.16 \times 10^4 + 7.34\}$; wherein T is temperature (K), provided that $293° K \leq T \leq 303° K$, and S is the rate of supersaturation.

It is a further aspect of the present invention to provide the method as described above, wherein the rate of supersaturation in the first supersaturated state in the step (A) is from 1.0 to 1.7, and said adding in step (B) occurs within 25 minutes after the first supersaturated state is achieved.

It is a further aspect of the present invention to provide a method of producing monosodium glutamate monohydrate comprising: a) converting α-form glutamic acid crystals produced in the method described above to β-form glutamic acid crystals, b) dissolving the β-form glutamic acid crystals produced in a) in a sodium hydroxide aqueous solution at a pH so that monosodium glutamate monohydrate forms, c) concentrating the solution to precipitate crystals, and d) drying the precipitated crystals.

According to the presently disclosed subject matter, α-form crystals of glutamic acid can be produced easily and stably in a short period of time.

BRIEF DESCRIPTION OF THE DRAWINGS

FIG. 1 depicts a diagram illustrating a two-step neutralization crystallization method.

FIG. 2 depicts a graph showing the relationship between the rate of supersaturation in the first neutralization step versus the time up to the second neutralization step. The form, either alpha or beta, of the deposited crystals is also shown. The overall rate of supersaturation is 8.0.

FIG. 3 depicts a graph showing the relationship between the rate of supersaturation in the first neutralization step versus the time up to the second neutralization step. The form, either alpha or beta, of the deposited crystals is also shown. The overall rate of supersaturation is 4.0.

FIG. 4 depicts a graph that shows when the β-form crystals appeared, based on temperature and rate of supersaturation. This result is based on the results of the experiments shown in FIGS. 2 and 3.

FIG. 5 depicts photographs of magnified glutamic acid crystals.

FIG. 6 shows spectra of glutamic acid crystals obtained in Example 1 and Comparative Example 1, measured by Raman spectrophotometry.

FIG. 7 is a graph depicting the particle size distribution of crystals obtained in Example 1 and Reference Example 1.

DETAILED DESCRIPTION OF EXEMPLARY EMBODIMENTS

In the crystallization method, an aqueous solution containing glutamic acid is prepared, and the volume of acid that neutralizes all of the glutamic acid in the solution is determined. If the total volume of the acid is added to a portion of the glutamic acid solution, the pH of the solution becomes lower than the isoelectric point of glutamic acid, which is pH 3.2. As shown in FIG. 1, the lower the pH is, the greater the solubility. Accordingly, when the initial glutamic acid concentration exceeds the solubility, supersaturation can be achieved. When the supersaturation in the first step is maintained at a given level, after a certain elapsed time period, β-form crystals or a mixture of α-form and β-form crystals will precipitate. Then, it is necessary to precipitate α-form crystals preferentially by achieving supersaturation in the second step before the precipitation of β-form crystals. For this purpose, the remainder of the glutamic acid aqueous solution is added to the supersaturated aqueous solution produced in the first step, which results in a second supersaturated state. Since the amount of acid that is necessary to adjust the solution to reach the isoelectric point of glutamic acid must be added to the solution, the pH of the solution becomes 3.2 at this time and achieves the maximum crystallization rate.

The initial glutamic acid concentration used in the crystallization method can be 50 g/l to 200 g/l, and in another example 80 to 120 g/l. The cation that forms a salt of glutamic acid in the glutamic acid salt solution is not limited, and can be an ammonium ion or sodium ion. The pH of the solution can be, in general, in the range of about 5.5 to 8.0, and in another example about 6.0 to 7.5. The glutamic acid salt solution can be a glutamic acid fermentation broth, a solution from which bacterial cells have been removed, and the like.

The acid that is added to the glutamic acid salt solution can be any acid which is able to function as an hydrogen ion donor, such as hydrochloric acid, sulfuric acid, and phosphoric acid. The volume of the acid to be added can be that which is sufficient to neutralize the glutamic acid which is dissolved in the glutamic acid salt solution, up to its isoelectric point of pH 3.2. Furthermore, the volume of added acid can be that which is sufficient to increase the final crystallization rate of glutamic acid, and is typically a volume which results in neutralization up to pH 3.2±3%, and in another example ±1%.

The glutamic acid salt solution described above can be divided into two portions, with one portion being used in the first supersaturation step of the method. The volume of the glutamic acid salt solution used in the first step can be that which results in a rate of supersaturation in the first supersaturation step of 1.0 to 1.7. If outside of the above range, β-form crystals will likely form within 25 minutes.

In typical crystallization methods, a highly concentrated solution of a solute to be precipitated is prepared, and then, the solubility of the solute in solution is lowered by adjusting the temperature, pH, or the like to supersaturate the solution. Such supersaturation becomes the driving force for the formation of crystals. The supersaturation results in a temporary dissolved state during crystallization, even though the concentration of the solute is higher than its solubility. The magnitude of the supersaturation is expressed in two ways. One is called the rate of supersaturation, and the other is called the degree of supersaturation. The rate of supersaturation is determined by dividing the actual concentration of a solute in its solution state by its solubility. The degree of supersaturation is the remainder obtained by subtracting the solubility from the actual concentration of a solute. Herein, the magnitude of supersaturation is expressed by the rate of supersaturation.

In order to calculate the rate of supersaturation in the first supersaturated state, the solubility of glutamic acid is calculated as follows. The temperature dependency of the solubility of glutamic acid is known ("Shokuhin Kogyo Handbook", p. 651-656, Kenpokusha, 2004), and can be approximated by the Clausius-Clapeyron's formula.

$$\text{Solubility at pH } 3.2(s)[\text{g}/100 \text{ g water}] = \exp\left[\frac{-3348.1}{T[^\circ \text{C.}] + 273} + 11.375\right]$$

Mathematical formula 1

The pH dependency of the solubility of glutamic acid is known ("Shokuhin Kogyo Handbook", p. 651-656, Kenpokusha, 2004), and can be determined by the following formula:

$$\text{Solubility}(s, \text{pH})[\text{g}/100 \text{ g water}] = \text{Solubility at pH } 3.2(S)[\text{g}/100 \text{ g water}] \times \frac{84.6}{\text{existing ration of Glu}^{\pm} \text{at each pH}}$$

Mathematical formula 2

Glu$^{\pm}$ represents glutamate ion with an electric charge of zero. The hydrogen ion dissociation constants are known to be pk$_1$=2.19, pk$_2$=4.25, pk$_3$=9.67, respectively ("Kagaku Binran", p. 432, Maruzen, 1993). Conversion of units from solubility per 100 g water to g/l is determined by the following formula:

$$\text{Solubility}(s, \text{pH})[\text{g}/100 \text{ g water}] = \frac{\text{Solubility}(s, \text{pH})[\text{g}/100 \text{ g water}]}{\text{Solubility}(s, \text{pH})[\text{g}/100 \text{ g water}] + 100} \times 1000 \times 1.06$$

Mathematical formula 3 provided that solid matter is glutamic acid alone, and that specific gravity is d=1.06 g/ml. Using the solubility values determined as above, the rate of supersaturation can be calculated. In FIG. 1, the rate of supersaturation in the first step (A) is represented by c/b, and the overall rate of supersaturation is represented by c/a. To determine the volume of aqueous glutamic acid salt solution that can be used to achieve the first supersaturated state, varying amounts of the glutamic acid salt solution can be added, and a calibration curve of the pH at each chosen volume can be prepared. Then, the volume required to attain the desired pH of the solution can be determined. That is, the pH that gives the desired rate of supersaturation is determined, and the volume necessary to achieve that pH can then be determined from the calibration curve, and this is often a pH range. Therefore, the range of the pH depends on the glutamic acid concentration of the aqueous solution prior to the formation and precipitation of the crystals. For example, the pH range corresponding to the range of the rate of supersaturation in the first supersaturated state of 1.0 to 1.7 is 1.3 to 1.6 at an overall rate of supersaturation of 8.0. During crystallization at an overall rate of supersaturation of 4.0, the pH range corresponding to the rate of supersaturation in the first supersaturated state of 1.0 to 1.7 is 1.7 to 2.0.

The first supersaturated state can be achieved by adding the acid to the glutamic acid salt solution, the volume of which is determined as described above. The temperature of the liquid solution can be between 20 and 30° C. The risk of β-form crystals precipitating increases when the temperature is higher or lower than these limits. The acid does not have to be added gradually, but may be added all at once. The solution can be stirred to homogenize it.

In order to form and precipitate α-form crystals preferentially, the remaining glutamic acid salt solution must be added within a definite time period after the first supersaturated state is achieved. This time period can be determined, for example, as follows:

100 ml of 127 g/l monosodium glutamate monohydrate (MSG) aqueous solution can be prepared, and 3.4 g of sulfuric acid can be placed in a separate beaker. The quantity of glutamic acid was 0.068 mole and sulfuric acid was 0.034 mole. For the first step, various volumes of the MSG aqueous solution was kept at 25° C. in a water bath while stirring with a magnetic stirrer, and the sulfuric acid was added to the solution all at once. For the second step, the remaining MSG aqueous solution can be added over varying time periods, but after reaching supersaturation. At that time, the overall rate of supersaturation was 8.0.

Whether α-form crystals or β-form crystals precipitate can be determined by observation through a microscope. When such a judgment is difficult, the crystal form can be determined by recrystallizing using the slurry as seed crystals. For example, a 127 g/l MSG solution was prepared, and 1 ml of the solution was removed. To this solution, about 200 μl sample was added. Thereafter, 20 μl concentrated sulfuric acid was added immediately, and shaken by hand. The resulting crystals were observed by a microscope to determine whether β-form crystals were present or not.

The metastable crystal (α-form crystal) of glutamic acid has a shape as shown in the photograph of FIG. 5 (a), and a chart produced during the analysis of the crystals by a Raman spectrometer is shown in FIG. 6(a). In FIG. 5(b), the flat crystals are the stable crystals. FIG. 6(b) shows the characteristic peaks.

The relationship between the rate of supersaturation during the first step and the time from the addition of sulfuric acid to the addition of the remaining MSG aqueous solution, and examination of the form of the precipitated crystals, that is, α-form or β-form were determined, and the results are shown in FIG. 2.

100 ml of 63.5 g/l sodium glutamate monohydrate (MSG) aqueous solution was prepared, and 1.7 g sulfuric acid was placed in a separate beaker. The quantity of glutamic acid was 0.034 mole and sulfuric acid was 0.017 mole in their respective solutions. For the first step of the method, varying amounts of the MSG aqueous solution was kept at 25° C. in a water bath while stirring by a magnetic stirrer, and the sulfuric acid was added all at once. For the second step, the remaining MSG aqueous solution can be added over varying time periods, but after reaching supersaturation. At that time, overall rate of supersaturation was 4.0. The crystal form was determined, and the results are shown in FIG. 3.

The time period from reaching supersaturation until β-form crystals precipitate is generally called the crystallization waiting time, and is determined by primary nuclei generation. The regions in FIG. 2 and FIG. 3 show the relationship between ln(t) (T: crystallization waiting time[sec.]) and $1/(T^3 \times (\ln S)^2)$ (T: temperature [K], S: rate of supersaturation [–]), and the results are shown in FIG. 4. As a result, the transition from region (1) and region (3) are not dependent on the system. That is, each region, i.e. (1) or (3), represents uniform primary nucleation or nonuniform primary nucleation, and β-form crystals precipitate as primary nuclei generation. The region (2) is considered to be the transition region, and it can be expressed by almost a straight line, although it varies according to experimental conditions. This can be shown by the range described below.

In FIG. 4, since it can be determined that the boundary line (1) has a slope of $3.46 \times 10^8$ and a y intercept of $-9.69$, the line (1) can be described by the following formula;

$$\ln t = 1/(T^3(\ln S)^2) \times 3.46 \times 10^8 - 9.69 \quad \text{Mathematical formula 4}$$

Since it can be determined that the boundary line (2) has a slope of $1.95 \times 10^7$ and a y intercept of 4.35, the line (2) (full line) is expressed by:

$$\ln t = 1/(T^3(\ln S)^2) \times 1.95 \times 10^7 + 4.35 \quad \text{Mathematical formula 5}$$

Since it can be determined that the boundary line (2) (dotted line) has a slope of $1.95 \times 10^7$ and a y intercept of 4.80, the line can be expressed by:

$$\ln t = 1/(T^3(\ln S)^2) \times 1.95 \times 10^7 + 4.80 \quad \text{Mathematical formula 6}$$

Since it can be determined that the boundary line (3) has a slope of $6.16 \times 10^4$ and a y intercept of 7.34, the boundary line (3) can be expressed by:

$$\ln t = 1/(T^3(\ln S)^2) \times 6.16 \times 10^4 + 7.34 \quad \text{Mathematical formula 7}$$

By referring to FIGS. 2 and 3, it can be deduced that in order to produce stable α-form crystals, the remaining glutamic acid salt solution can be added within:

when the rate of supersaturation to reach the first supersaturated state is 2.6 to 8.0, $t \leq \exp\{1/(T^3(\ln S)^2) \times 3.46 \times 10^8 - 9.69\}$;

when the rate of supersaturation to reach the first supersaturated state is 1.8 to 2.6, $t \leqq \exp\{1/T^3(\ln S)^2 \times 1.95 \times 10^7 + 4.35\}$; and when the rate of supersaturation to reach the first supersaturated state is 1.0 to 1.8, $t \leqq \exp\{1/T^3(\ln S)^2 \times 6.16 \times 10^4 + 7.34\}$.

However, in order to reach the first supersaturated state, it is necessary to wait at least 1 minute after adding the acid to the glutamic acid salt solution, before adding the remaining glutamic acid salt solution.

The remaining glutamic acid salt solution can also be added all at once, and at that time, it can be stirred.

It was found that the particle size distribution of crystals produced by this crystallization method is very fine compared with those produced by the conventional method of adding seed crystals. In general, when produced crystals are used as seed crystals, the greater the surface area of the crystals, the greater the effects. This is advantageous when using this crystallization method in a large-scale crystallization, and the like.

Therefore, the α-form crystal slurry thus produced can be used as seed crystals in a large-scale crystallization, and furthermore, the following transition crystallization can be conducted. That is, the solubility of the α-form crystals is necessarily higher than the solubility of the β-form crystals in the range from 0° C. to about 100° C. Then, when β-form seed crystals are added, or there is a certain probability that β-form crystals will occur suddenly, the solubility of the whole system becomes the solubility where the liquid bottom body is in the β-form. Then, α-form crystals dissolve, and are all converted to β-form crystals utilizing the solubility difference between the α-form crystal and β-form crystal as the driving force. After β-form glutamic acid crystals are obtained, they are dissolved by adjusting the pH so that monosodium glutamate monohydrate (MSG) is formed by an aqueous sodium hydroxide solution, and concentrated to precipitate the crystals. The crystals are separated and dried and can be used to manufacture commercial products of sodium glutamate monohydrate ("Shokuhin Kogyo Handbook", p. 651-656, Kenpokusha, 2004).

EXAMPLE 1

100 ml of 127 g/l monosodium glutamate monohydrate (MSG) aqueous solution was prepared, and 3.4 g of sulfuric acid was placed in a beaker. As a result, the quantity of glutamic acid was 0.068 mole, and sulfuric acid was 0.034 mole. 46 ml of the MSG aqueous solution was kept at 25° C. in a water bath while stirring with a magnetic stirrer, and the sulfuric acid was added all at once. The rate of supersaturation in this first step was 1.2. After 1.0 minute, the second supersaturation step was initiated by adding the remaining MSG aqueous solution of 54 ml to complete crystallization. At that time, the overall rate of supersaturation was 8.0, and crystals were in the α-form.

COMPARATIVE EXAMPLE 1

100 ml of 127 g/l monosodium glutamate monohydrate (MSG) aqueous solution was prepared, and 3.4 g of sulfuric acid was placed in a beaker. The quantity of glutamic acid was 0.068 mole and sulfuric acid was 0.034 mole. 54 ml of the MSG aqueous solution was kept at 25° C. in a water bath while stirring with a magnetic stirrer, and the sulfuric acid was added all at once. The rate of supersaturation in this first step was 2.3. After 2.5 minutes, the second supersaturation step was initiated by adding the remaining MSG aqueous solution of 46 ml. At that time, the overall rate of supersaturation was 8.0, and the crystals were in both the α-form and the β-form.

REFERENCE EXAMPLE 1

100 ml of 127 g/l monosodium glutamate monohydrate (MSG) aqueous solution was prepared, and 3.4 g of sulfuric acid was placed in a beaker. The quantity of glutamic acid was 0.068 mole and sulfuric acid was 0.034 mole. Sulfuric acid was gradually added to the MSG aqueous solution to adjust the pH to 5.0, 1 g of α-form crystals were added as seed crystals. After stirring the solution for 30 minutes, the remaining sulfuric acid was added over a 3 hour time period to precipiate glutamic acid crystals in the α-form.

INDUSTRIAL APPLICABILITY

According to the invention, α-form crystals of glutamic acid can be produced easily and stably, and can be incorporated into a manufacturing process of glutamic acid.

While the invention has been described in detail with reference to exemplary embodiments thereof, it will be apparent to one skilled in the art that various changes can be made, and equivalents employed, without departing from the scope of the invention. Each of the aforementioned documents is incorporated by reference herein in its entirety.

What is claimed is:

1. A method of producing α-form glutamic acid crystals comprising:
   (A) adding an acid to a first glutamic acid salt solution until the pH of the solution is 1.3 to 2.0;
   (B) waiting at least one minute until the solution has reached a first supersaturated state having a rate of supersaturation of 1.0 to 1.7; and
   (C) adding a second glutamic acid salt solution to the solution of (B) until the pH rises to the isoelectric point of glutamic acid and the solution reaches a second supersaturated state.

2. The method of claim 1, wherein said adding in step (C) occurs within 25 minutes after the first supersaturated state is achieved.

3. A method of producing monosodium glutamate monohydrate comprising:
   a) converting α-form glutamic acid crystals produced in the method of claim 1 to β-form glutamic acid crystals,
   b) dissolving the β-form glutamic acid crystals produced in a) in a sodium hydroxide aqueous solution at a pH so that monosodium glutamate monohydrate forms,
   c) concentrating the solution to precipitate crystals, and
   d) drying the precipitated crystals.

4. The method of claim 1, further comprising:
   forming a glutamic acid salt solution; and
   dividing said glutamic acid salt solution into said first glutamic acid salt solution and said second glutamic acid salt solution;
   wherein said adding a second glutamic acid salt solution renders a pH of 3.2 which is the isoelectric point of glutamic acid.

* * * * *